(12) United States Patent
Katoh et al.

(10) Patent No.: US 7,416,538 B2
(45) Date of Patent: *Aug. 26, 2008

(54) WALKING ASSISTANCE DEVICE

(75) Inventors: Hisashi Katoh, Wako (JP); Taiji Koyama, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/557,480

(22) PCT Filed: May 20, 2004

(86) PCT No.: PCT/JP2004/006828

§ 371 (c)(1),
(2), (4) Date: Jun. 23, 2006

(87) PCT Pub. No.: WO2004/103250

PCT Pub. Date: Dec. 2, 2004

(65) Prior Publication Data

US 2007/0027409 A1    Feb. 1, 2007

(30) Foreign Application Priority Data

May 21, 2003 (JP) ............................. 2003-143506

(51) Int. Cl.
*A61F 5/00* (2006.01)
*A61F 2/74* (2006.01)
*A61F 2/60* (2006.01)
*A61F 2/68* (2006.01)

(52) U.S. Cl. ............................. 602/16; 602/26; 602/23; 623/27; 623/28; 623/30; 623/31; 623/39; 623/40; 623/43

(58) Field of Classification Search .................. 602/16, 602/26, 23; 623/27, 28, 30, 31, 39, 40, 43

See application file for complete search history.

(56) References Cited

U.S. PATENT DOCUMENTS

| 2,010,482 | A | * | 8/1935 | Cobb | ........................... | 623/31 |
| 5,476,441 | A | * | 12/1995 | Durfee et al. | ................. | 602/23 |
| 5,588,456 | A | * | 12/1996 | Hart | ........................... | 135/67 |

(Continued)

FOREIGN PATENT DOCUMENTS

JP   58-163364   9/1983

(Continued)

*Primary Examiner*—Patricia Bianco
*Assistant Examiner*—Tarla Patel
(74) *Attorney, Agent, or Firm*—Squire, Sanders & Dempsey

(57) ABSTRACT

There is provided a walking assistance device equipped with an assisting force generator disposed on a side of each of a hip joint and a knee joint, comprising: a hip support member (1) having an attachment means (hip drive source mount 9) capable of repeatedly attaching and detaching a hip joint assisting force generator (hip joint actuator 10); a lower leg support member (2) having an attachment means (knee drive source mount 27) capable of repeatedly attaching and detaching a knee joint assisting force generator (knee joint actuator 26); and a drive unit (3) formed by integrally joining the hip joint assisting force generator and the knee joint assisting force generator via a link bar (25), wherein after the hip support member and the lower leg support member are fitted on a user's body, the assisting force generators of the drive unit are connected to the corresponding attachment means.

3 Claims, 7 Drawing Sheets

U.S. PATENT DOCUMENTS

| | | | |
|---|---|---|---|
| 6,821,233 B1 * | 11/2004 | Colombo et al. | 602/23 |
| 2002/0082711 A1 * | 6/2002 | Kuhn et al. | 623/27 |
| 2005/0283102 A1 * | 12/2005 | Schwenn et al. | 602/5 |
| 2007/0010378 A1 * | 1/2007 | Katoh et al. | 482/105 |
| 2007/0055189 A1 * | 3/2007 | Katoh et al. | 602/16 |

FOREIGN PATENT DOCUMENTS

| | | |
|---|---|---|
| JP | 61-228854 | 10/1986 |
| JP | 9-103443 | 4/1997 |
| JP | 09-103443 | 4/1997 |
| JP | 09-271496 | 10/1997 |
| JP | 9-271496 | 10/1997 |
| JP | 10-248987 | 9/1998 |
| JP | 11-508167 | 7/1999 |
| JP | 11-290360 | 8/1999 |
| JP | 11-290360 | 10/1999 |
| JP | 2001-214303 | 8/2001 |
| WO | WO9700661 | 1/1997 |

\* cited by examiner

WALKING ASSISTANCE DEVICE

TECHNICAL FIELD

The present invention relates to a walking assistance device for providing an assisting force to the movement of the nip joint and knee joint.

BACKGROUND ART

Various proposals have been made for a walking assistance device that is adapted to mount an actuator to the hip joint or knee joint of a person having a walking impediment due to injury, disease or weakened muscle resulting from aging, so that the power from the actuator can be used to assist the movement of the lower limb.

Conventionally, in such a walking assistance device, it was necessary to fasten corset-like support members onto the hip, thigh and lower leg portions to securely mount rotational actuators on a side of the hip joint and knee joint and transmit the drive torque from the rotational actuators to the lower limb.

Patent Publication 1: JPA No. 58-163364 (FIGS. 1-4)

DISCLOSURE OF THE INVENTION

Objects to be Achieved by the Invention

However, the prior art devices, such as those disclosed in the above publication, were quite cumbersome to put on, and it was practically impossible for a one having a leg impediment to put on the support member by oneself.

The present invention was made to solve such a prior art problem and a primary object of the present invention is to provide a walking assistance device that can be adjusted to an individual user's build and worn by the user easily and securely.

MEANS TO ACHIEVE THE OBJECTS

In order to achieve such an object, according to the invention of claim 1, there is provided a walking assistance device comprising an assisting force generator disposed on a side of each of a hip joint and a knee joint to provide an assisting force to a movement of a lower limb, comprising: a hip support member (1) having an attachment means (hip drive source mount 9) capable of repeatedly attaching and detaching a hip joint assisting force generator (hip joint actuator 10); a lower leg support member (2) having an attachment means (knee drive source mount 27) capable of repeatedly attaching and detaching a knee joint assisting force generator (knee joint actuator 26); and a drive unit (3) formed by integrally joining the hip joint assisting force generator and the knee joint assisting force generator via a link bar (25), wherein after the hip support member and the lower leg support member are fitted on a user's body, the assisting force generators of the drive unit are connected to the corresponding attachment means.

In this way, the walking assistance device can be formed by combining three separate members, and this makes it easier for the walking assistance device to be worn by a user. The three members can be chosen individually and this allows the walking assistance device to easily cope with differences in build or condition (degree of impediment) of the users.

According to the invention of claim 2, the hip support member comprises: a back support (4) extending from right and left iliac crests to a backside of a sacroiliac joint; and a pair of web parts (15) extending out from either right and left ends of the back support and connected to each other with a buckle (16) at a lower abdominal portion around a lower part of an abdominal muscle. In such a structure, it is possible to fasten the hip support member on the user's body easily and securely by just adjusting the tension of the web parts as desired. Further, because there is no part that needs to be fastened on the thigh, the hip support member can be easily worn to the hip of the user even while sitting on a chair.

According to the invention of claim 3, the lower leg support member (2) comprises a band-like member (24) wound around a leg so as to extend from lateral sides of an anterior tibial muscle to a region between a lower part of a calf muscle and an upper part of the Achilles tendon. Thus, because the lower leg support member is worn on the portion of the leg where there is a small amount of movement of the muscle, the support member can be firmly fastened to the lower leg while reducing discomfort to the user.

BEST MODE FOR CARRYING OUT THE INVENTION

In the following, the present invention will be described in detail with reference to the appended drawings.

FIG. 1 shows a walking assistance device of the present invention as worn on a user's body. The walking assistance device consists of a hip support member 1, lower leg support member 2 and a drive unit 3, where the hip support member 1 and the lower leg support member 2 are secured on a lower limb and a rotational torque generated by the drive unit 3 is transmitted to the lower limb via the hip and lower leg support members, to whereby provide a force for supplementing a reduced muscle power.

The hip support member 1 comprises a back support 4, belt portion 5 and lining portion 6, as shown in FIG. 2.

Additionally referring to FIG. 3, the back support 4 is substantially of the shape of letter-U as seen in plan view so that it abuts a region of the body extending from right and left iliac crests (front ends of the pelvic bone) 7 to the backside of the sacroiliac joint (joint between the vertebrae and pelvic bone) 8, and consists of a substantially rigid body so as to withstand the drive force generated by a hip joint actuator 10, which consists of an electric motor equipped with a reduction gear or the like and is mounted on a hip drive source mount 9 provided at each of the right and left ends of the back support 4. A rear portion of the back support 4 has a hollow space so that a control circuit and a battery for supplying electric power to the control circuit as well as to the electric motor are accommodated therein, though not explicitly shown in the drawings. Further, at a portion of the back support 4 that directly abuts the user's body is provided a cushioning pad 11.

The belt portion 5 is made of a relatively rigid material and comprises: a pair of right and left bases 14 integrally attached by means of bolts to inner sides of belt joints 13 provided at right and left side portions of the back support 4; a pair of right and left web parts 15 fixed to front ends of the bases 14; and a pair of right and left buckles 16 attached to front ends of the web parts 15. The inner surface of the belt portion 5, i.e., the surface facing the hip portion of the user's body, is adapted to be attached with the lining portion 6 for protection by means of loop and hook fastener or the like.

The cushioning pad 11 provided to the back support 4 comprises a center pad 18 abutting a depression extending along a lumbar vertebra 17 and a pair of side pads 19 abutting laterally outer regions of erector spinae muscles slightly jutting out backward at right and left of the lumbar vertebra 17.

Further, the lining portion 6 comprises iliac pads 20 abutting the iliac crests 7. Thus, a total of five pads abut principal portions of the hip to keep the back support 4 from moving out of place. Further, because direct contact of the hip drive source mount 9 with the user's body would cause pain to the user and could impart a large impact on the body if the user happens to fall, hip joint pads 21 are provided to the lining portion 6 so as to be interposed between the user's body and the hip drive source mount 9 and reduce the impact and pain.

Each of the web parts 15 comprises a pair of upper and lower plain weave belts secured to the associated base 14, and the front ends of the belts are joined together and attached to the corresponding buckle 16 so that they form a shape of letter-V that converges in the front direction. The upper belt 15U of each web part 15 extends from the joint with the base 14 disposed at a position corresponding to the iliac crest 7 toward the buckle 16 disposed at an intermediate portion ("tanden") between the navel and pubic bone along a direction of the extension of muscle fibers of the abdominal external oblique muscle. The lower belt 15L of the web part 15 extends from the joint with the base 14 disposed on a side of the hip joint toward the buckle 16 along a direction of fibers of the abdominal internal oblique muscle.

The upright posture of the spine is maintained by the balance of back muscle, pectoral muscle and abdominal muscle. The weakening of muscles of a person having walking impediment applies not only to the muscles of lower limb but also to the back, pectoral or abdominal muscles. Particularly, the weakening of the abdominal muscle can lower the abdominal cavity and cause the spine to bend in the shape of letter-S as seen in side view, thus making it difficult to maintain the upright posture during walking. According to the device of the present invention, the buckle 16 is positioned at a center of lower abdomen called "tanden" where the rectus abdominis muscle, abdominal external oblique muscle, abdominal internal oblique muscle, transversus abdominis muscle, etc. which play an important role in keeping the upright posture, overlap each other, and a tightening force is applied to the web parts 15 so that the back support 4 fitted on a region extending from the right and left iliac crests 7 to the backside of the secroiliac joint functions to correct the curve of the spine and stabilize the pelvis to achieve a proper posture and at the same time increase the abdominal cavity pressure to lift up the viscera to proper positions. Further, because the web parts 15 abut the lower abdominal portion with a relatively large contact area, the pressure applied to the abdominal cavity can be distributed evenly over the whole lower abdominal portion, thus reducing the uncomfortable pressure felt by the user.

On the other hand, as also shown in FIG. 4, the lower leg support member 2 comprises a band-like member 24 wound around the region where the skin movement is relatively small during motion of the lower limb joints, i.e., region extending from lateral sides of an upper part of the anterior tibial muscle to the portion between a lower part of the calf muscle 22 and an upper part of the Achilles tendon 23. According to such a structure, it can be avoided to place the principal engagement points of the lower leg support member 2 on the calf, of which circumferential length can vary with the extension/flexion of the knee, or on the Achilles tendon where the skin moves with the motion of the ankle, and therefore it is possible to securely fasten the lower leg support member 2 on the lower leg with an abundant tightening force.

Additionally referring to FIG. 5, the drive unit 3 comprises a hip joint actuator 10 and a knee joint actuator 26, each consisting of an electric motor equipped with a reduction gear, where the actuators are attached to either end of a link bar 25 which is expandable and contractable in a telescopic fashion. The drive unit 3 is adapted so as to be able to repeatedly attached to and detached from the hip drive source mount 9 provided to the hip support member 1 at a position corresponding to a side of the hip joint as well as from a knee drive source mount 27 provided to the lower leg support member 2 at a position corresponding to a side of the knee joint.

As shown in FIG. 6, the hip drive source mount 9 comprises: a base plate 31 attached to a vicinity of the rigid belt joint 13 via a link plate 30; a slide plate 32 overlapping the inner surface of the base plate 31 so as to be slidable within a prescribed range; an operation lever 35 supported by an inner cover 33 via a pin shaft 34, the inner cover 33 being integrally attached to the base plate 31; and a link 36 for interconnecting the slide plate 32 and the operation lever 35. As also shown in FIG. 7, the operation lever 35 is adapted to be pivotable around its middle portion which is pivoted by the pin shaft 34 such that the lever 35 can move between a laid down position and an upright position for a range of about 90 degrees.

The base plate 31 is formed with four round holes 37 at positions dividing a circle into four equal parts. The slide plate 32 is formed with four larger holes 38 having a same diameter and are located at same positions as the round holes 37, and four smaller elongated holes 39 extending out from associated larger holes 38 in the same direction, wherein the four larger holes 38 and four elongated holes 39 are integrated to form four figure 8 shaped holes 40.

A side of the hip joint actuator 10 facing the hip drive 9 is provided with four pins 41 standing thereon, the pins 41 corresponding to the four round holes 37 formed in the base plate 31. The pins 41 each consist of a larger diameter head portion 42 having a substantially same diameter as the round hole 37 and a shaft portion 43 having a diameter substantially same as the width of the elongated hole 39.

When the operation lever 35 is in the upright position, the larger holes 38 of the figure 8 shaped holes 40 are aligned with the round holes 37. Therefore, as the four pins 41 of the hip joint actuator 10 are inserted into the round holes 37 of the base plate 31, the head portions 42 of the pins 41 pass through the larger holes 38 and protrude from an inner surface of the slide plate 32. In this state, by bringing down the operation lever 35, the slide plate 32 connected to the operation lever 35 via the link 36 is caused to slide so that the elongated holes 39 of the slide plate 32 engage the shaft portions 43 of the pins 41 and the head portions 42 keep the pins 41 from being pulled out from the elongated holes 39. In this way, the hip joint actuator 10 can be attached to or detached from the hip drive source mount 9 with a so-called single touch operation.

On the other hand, as shown in FIG. 8, the knee drive source mount 27 is attached by screws, for example, to a connection piece 2a integrally formed in an upper end of the lower leg support member 2. The knee drive source mount 27 is integrally formed with a pair of engagement arms 27a where a free end of each engagement arm 27a is formed with a lock finger 52. Between the pair of engagement arms 27a is formed a resilient arm 27b to extend in the same direction as the engagement arms 27a, where the resilient arm 27b has a small thickness to be resiliently deformable.

The knee joint actuator 26 is provided with a latch portion 51 for engaging the lock fingers 52 of the knee drive source mount 27 to thereby attach the knee joint actuator 26 to the lower leg support member 2. As shown in FIG. 9, the latch portion 51 is provided with a slot 51b into which the pair of engagement arms 27a and resilient arm 27b, which are integrally formed to the knee drive source mount 27, can be inserted. Inside the slot 51b is provided a resilient engagement piece 51a having a free end extending obliquely upward so as to engage the lock fingers 52 at an underside (as seen in FIG. 9) of the inserted pair of engagement arms 27a.

As the engagement arms 27a and the resilient arm 27b are inserted in the slot 51b of the latch portion 51, the advancement of the lock fingers 52 causes the resilient engagement piece 51s to flex downward as seen in FIG. 9. When the lock fingers 52 reach a predetermined position inside the slot 51b, the resilient engagement piece 51a moves back upward so that its free end engages the lock fingers 52 to lock the engagement arm 27a in the slot 51b.

The locking engagement in the latch mechanism structured as above can be released by pressing a press button provided on the outer surface of the latch portion 51. Specifically, when the button 53 is pressed downward as seen in FIG. 9, the resilient engagement piece 51a is pressed via the resilient arm 27b so that its free end deflects downward as indicated by an arrow in FIG. 9. This releases the engagement between the resilient engagement piece 51a and the lock fingers 52. Thus, the lower leg support member 2 can be detached from the knee joint actuator 26 by a so-called single touch operation.

The above structured walking assistance device of the present invention comprises the hip support member 1, lower leg support member 2 and drive unit 3 as separate members, and therefore, when a person having impediment in lower limbs wishes to put on the device, the person can do it even while the person is sitting on a chair, for example. Specifically, the hip support member 1 can be worn easily by making the back support 4 abut the backside of the hip portion and pulling the both web parts 15 toward the lower abdominal part to fasten the buckle 16 and then properly adjusting the tension of the web parts 15. The lower leg support member 2 can be worn just by winding it around a lower part of the calf.

The drive unit 3 can be worn on the body by placing the link bar 25 to extend along the side of the thigh and attaching the actuators 10, 26 to the respective drive source mounts 9, 27 of the already worn support members 1, 2 with a single touch operation. Thus, the attachment and detachment of the walking assistance device can be achieved easily without need for the wearer to take an unnatural posture and without need for help of other people.

If the device of the present invention is worn over a spat S for exercise that is adapted to provide a specific muscle(s) with a tightening force that is equivalent to that produced by taping (see Japanese Patent Application Laid-Open No. 2001-214303), the device can function even more effectively to improve the motion ability of the user in cooperation with the muscle support effect resulting from the tightening force produced by the fibers forming the spat S. Also, if the drive torque is effected in reverse, the device of the present invention can apply a load torque upon the joint, and therefore the device can be used not only as a motion assisting device but also as a load generator for medical treatment, rehabilitation or training for muscle development.

INDUSTRIAL APPLICABILITY

As described above, according to the present invention, the following advantages can be obtained:

1. Owing to the structure that the walking assistance is constituted by three separate members, i.e., a hip support member having a hip drive source mount capable of repeatedly attaching and detaching a hip joint actuator; a lower leg support member having a knee drive source mount capable of repeatedly attaching and detaching a knee joint actuator; and a drive unit formed by integrally joining the two actuators via a link bar, the walking assistance device can be worn by a user easily because the three members can be put on individually. Further, because the three members can be chosen individually, the walking assistance device is allowed to easily cope with differences in build or condition of the users.

2. Because the hip support member comprises a back support fitted to the back portion of the body and a pair of web parts extending out from either right and left ends of the back support and connected to each other with a buckle at a lower abdominal portion, it is possible to adjust the fit of the hip support member as desired by just adjusting the tension of the web parts. Further, because there is no part that needs to be fastened on the thigh, the hip support member can be easily worn to the hip of the user even while sitting on a chair.

3. Owing to the structure where the lower leg support member comprises a band-like member wound around a leg so as to extend from lateral sides of an anterior tibial muscle to a region between a lower part of a calf muscle and an upper part of an Achilles tendon, the lower leg support member can be worn on the portion of the leg where there is a small amount of movement of the muscle, and therefore, the support member can be firmly fastened to the lower leg while reducing discomfort to the user.

BRIEF DESCRIPTION OF THE DRAWINGS

Now the present invention is described in the following with reference to the appended drawings, in which.

Figure 1:
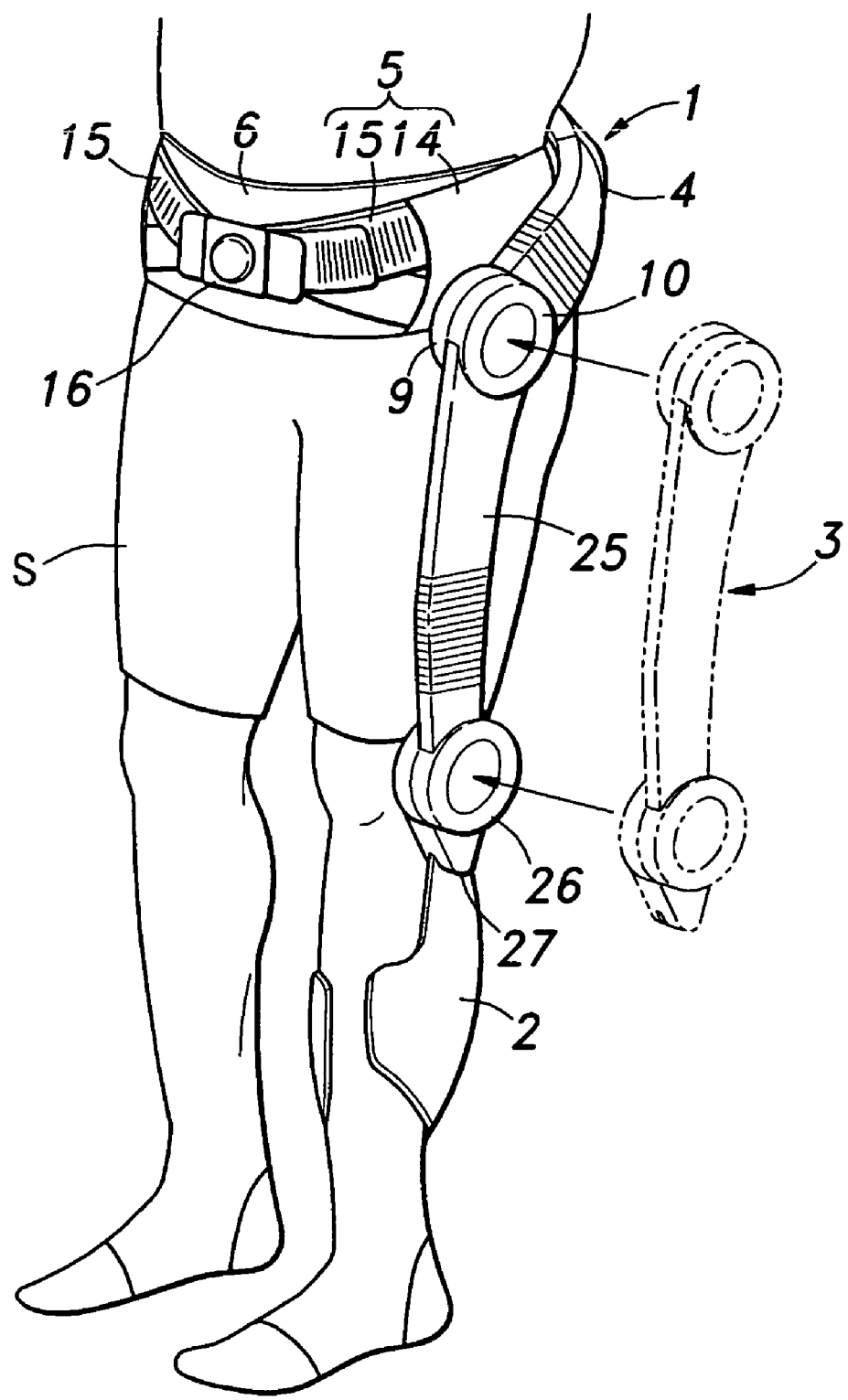
FIG. 1 is a perspective view showing a lower body on which a walking assistance device of the present invention is fitted.
Figure 2:
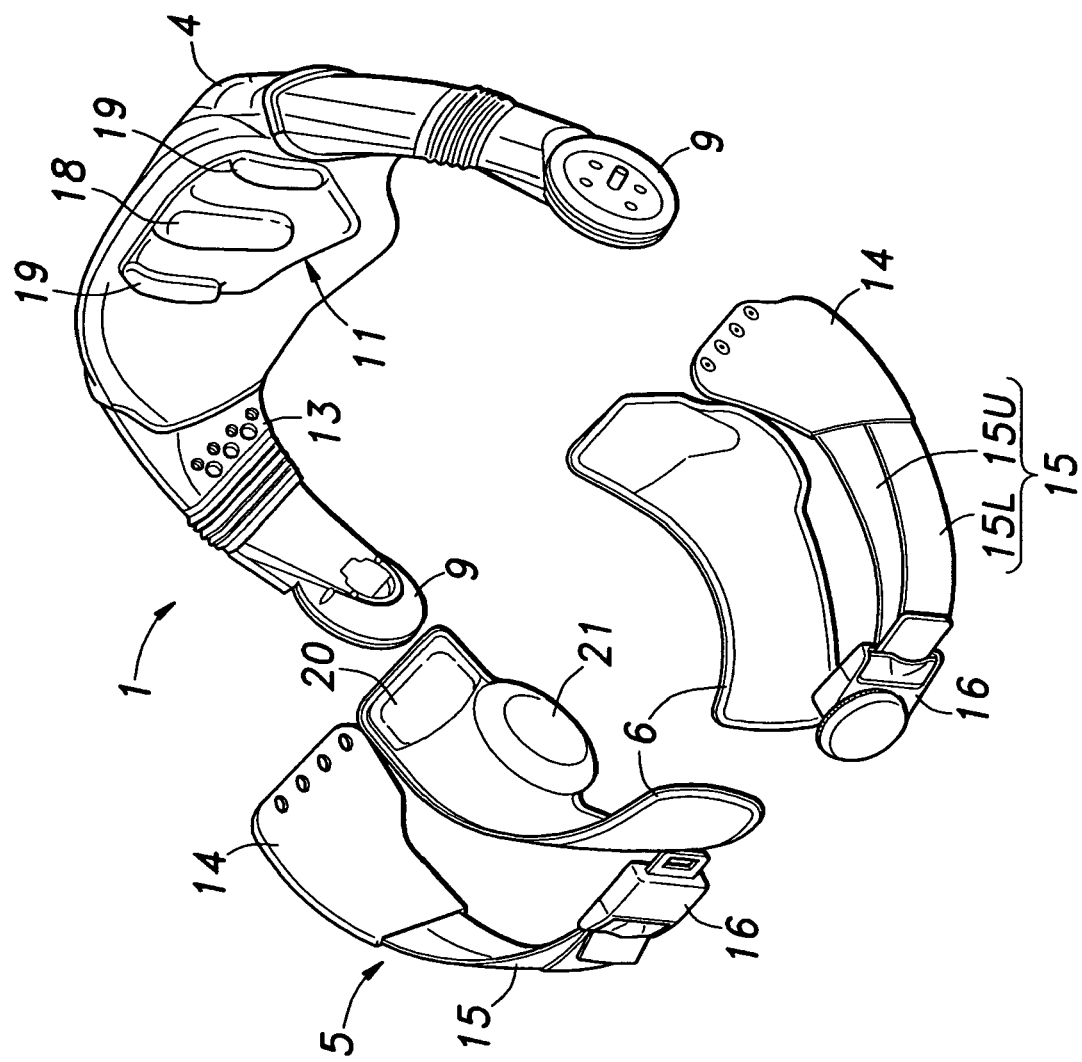
FIG. 2 is an exploded perspective view showing the structure of a hip support member of the walking assistance device according to the present invention.
Figure 3:
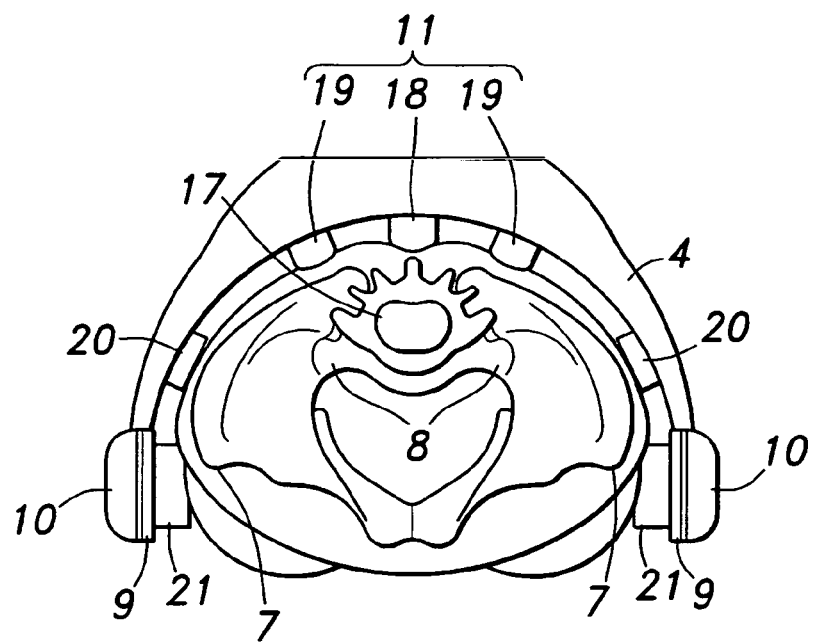
FIG. 3 is an explanatory drawing showing the relationship between a back support and the user's body.
Figure 6:
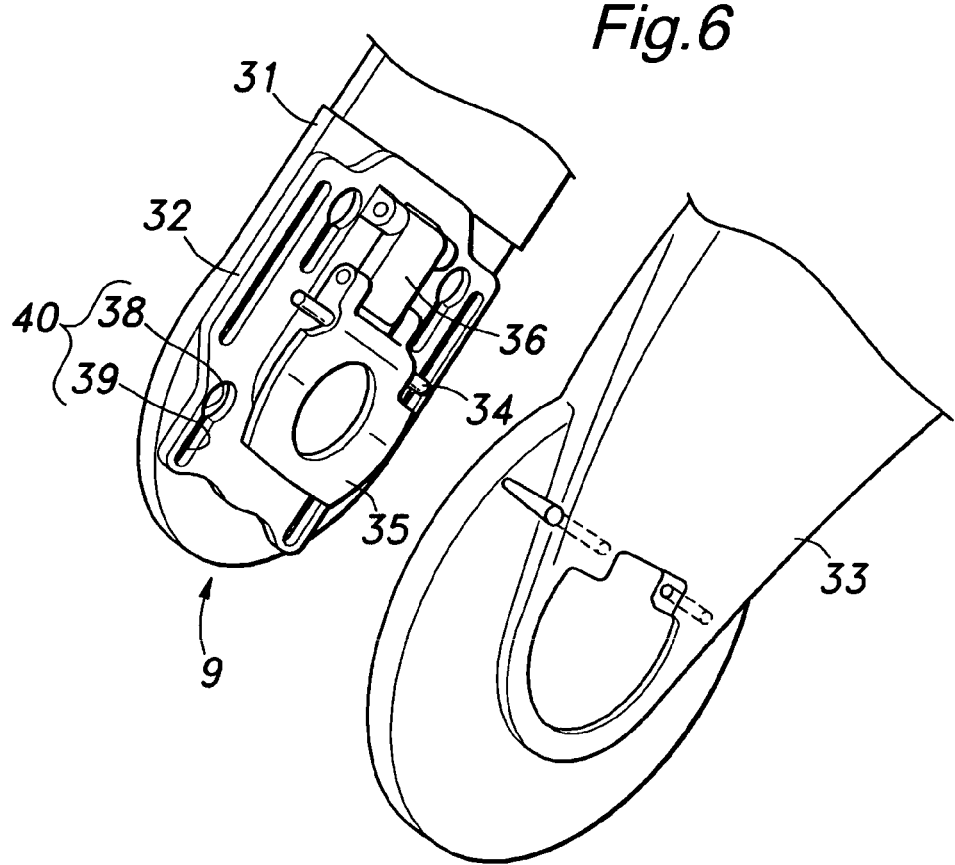
FIG. 6 is a perspective view of the hip joint drive source mount.
Figure 4:
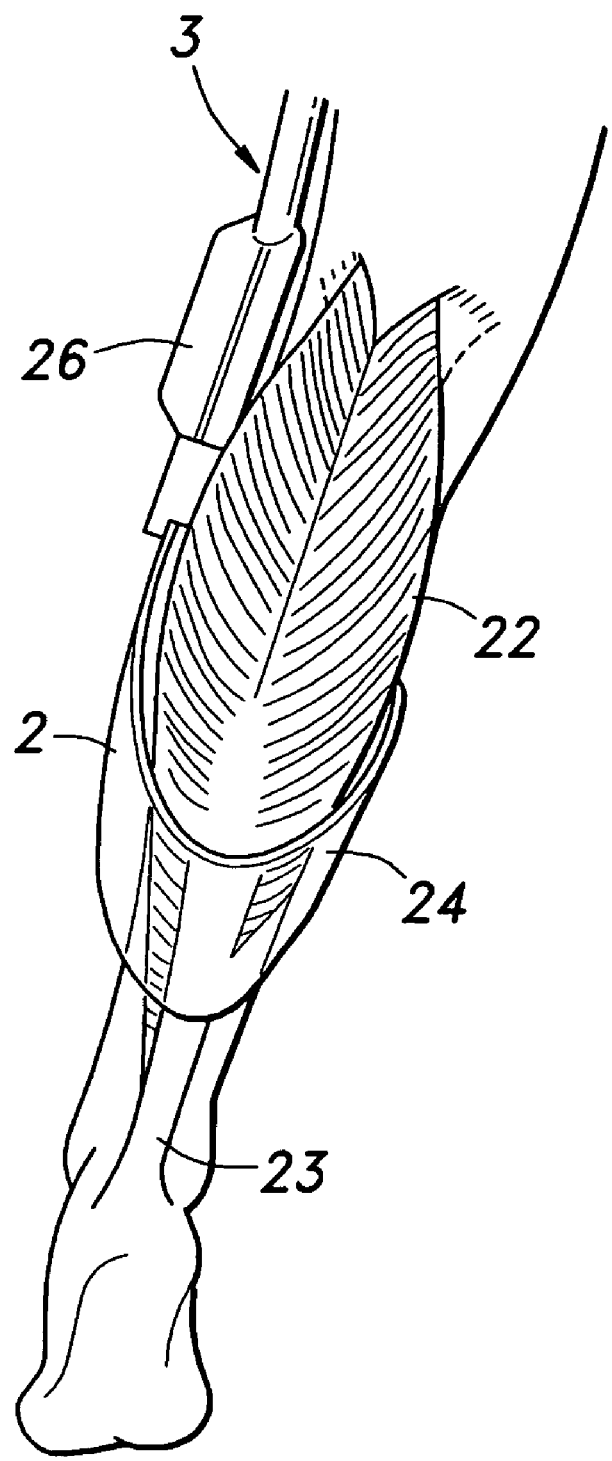
FIG. 4 is an explanatory drawing showing a lower leg support member fitted on a lower leg portion.
Figure 5:
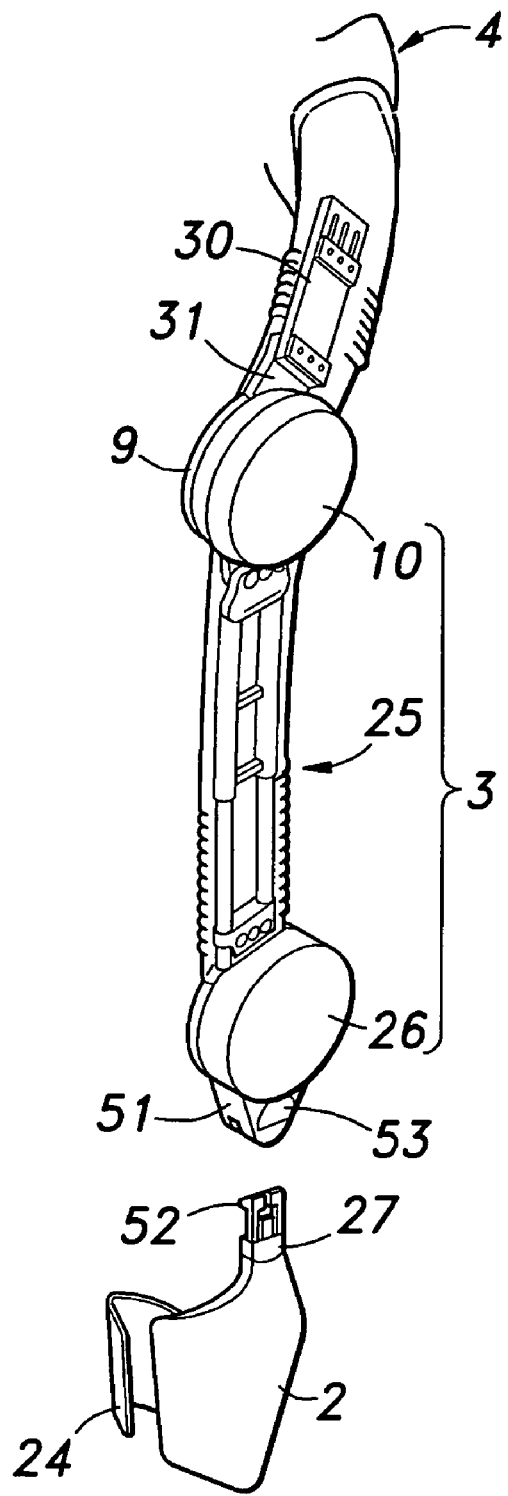
FIG. 5 is a perspective view of a principal part of the walking assistance device according to the present invention.
Figure 7:
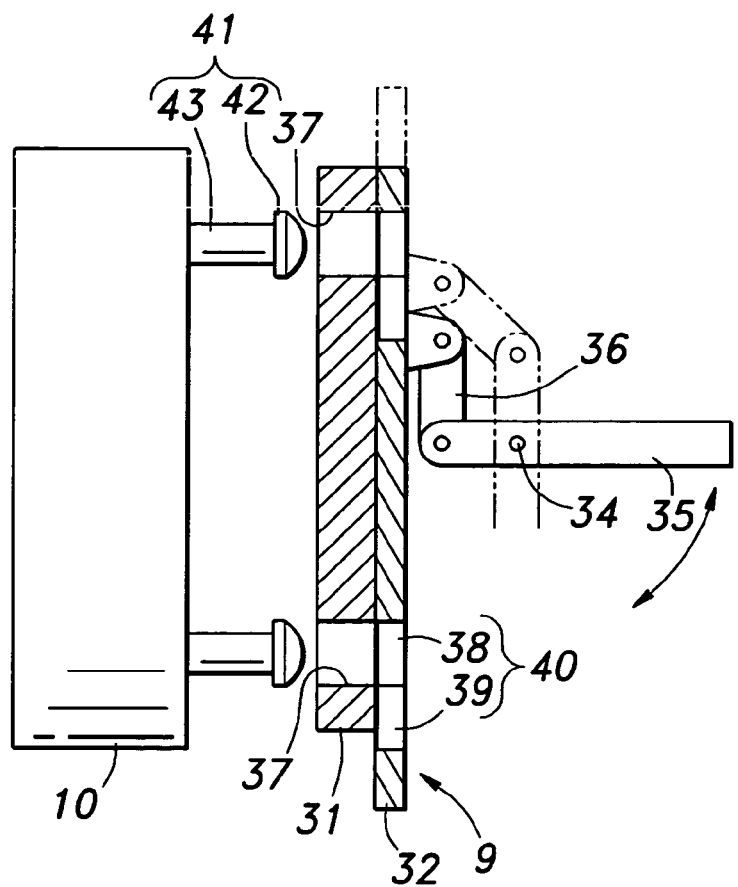
FIG. 7 is a view for explaining a way of operating the hip joint drive source mount.
Figure 8:
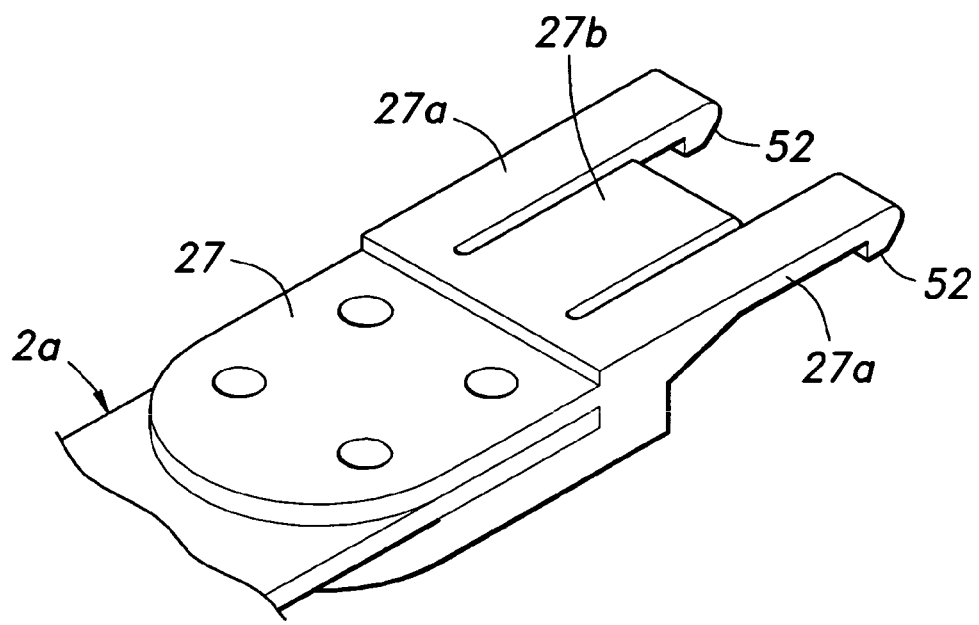
FIG. 8 is a perspective view of the knee drive source mount.
Figure 9:
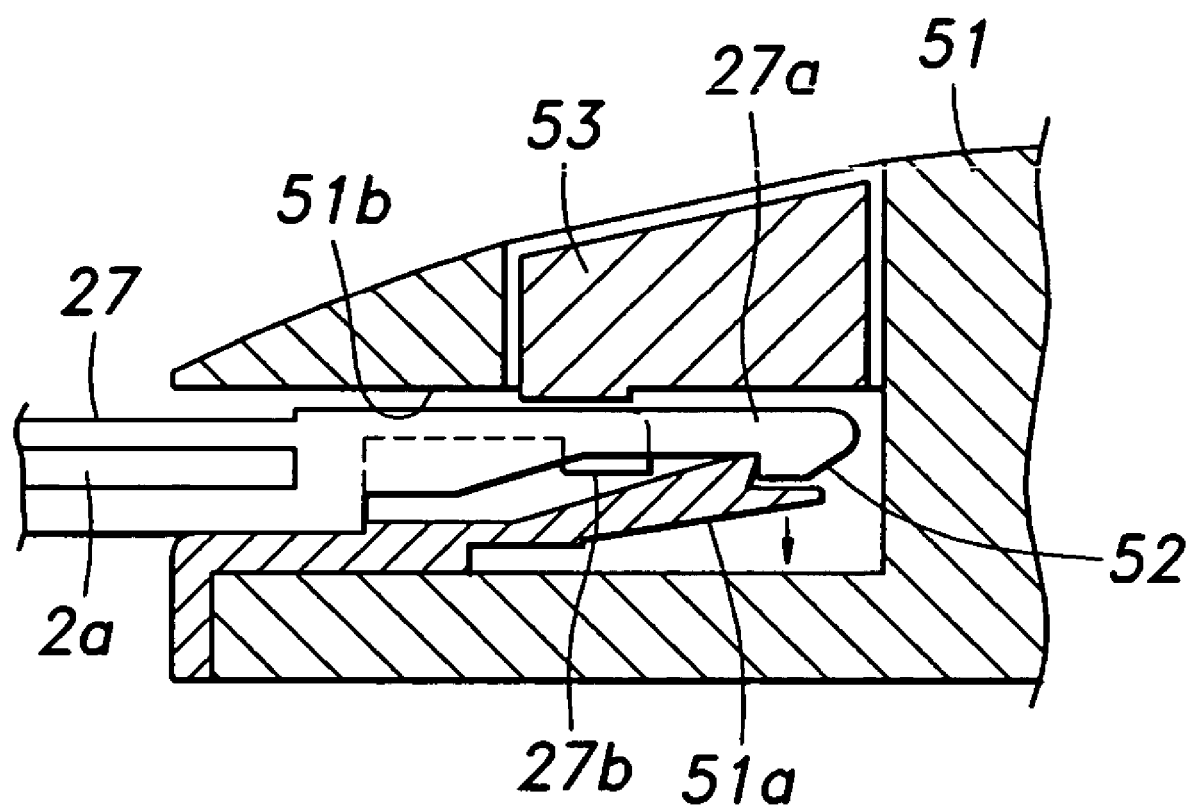
FIG. 9 is a longitudinal cross sectional view showing the latch portion of the knee joint actuator in a state connected to the knee drive source mount.

DESCRIPTION OF THE REFERENCE NUMERALS 1 hip support member
2 lower leg support member
3 drive unit
4 back support
9 hip drive source mount
10 hip joint actuator
15 web part
16 buckle
24 band-like member
25 link bar
26 knee joint actuator
27 knee drive source mount

The invention claimed is:

1. A walking assistance device comprising an assisting force generator disposed on a side of each of a hip joint and a knee joint to provide an assisting force to a movement of a lower limb, comprising:
   a hip support member having an attachment means capable of repeatedly attaching and detaching a hip joint assisting force generator;
   a lower leg support member having an attachment means capable of repeatedly attaching and detaching a knee joint assisting force generator; and
   a drive unit formed by integrally joining the hip joint assisting force generator and the knee joint assisting force generator via a link bar,
   wherein the hip support member, the lower leg support member and the drive unit are separate members from each other and are joined together by attaching the hip joint assisting force generator to the attachment means of the hip support member and attaching the knee joint assisting force generator of the drive unit to the attachment means of the lower leg support member.

2. The walking assistance device according to claim 1, wherein the hip support member comprises: a back support extending from right and left iliac crests to a backside of a sacroiliac joint; and a pair of web parts extending out from either right and left ends of the back support and connected to each other with a buckle at a lower abdominal portion around a lower part of an abdominal muscle.

3. The walking assistance device according to claim 1, wherein the lower leg support member comprises a band-like member wound around a leg so as to extend from lateral sides of an anterior tibial muscle to a region between a lower part of a calf muscle and an upper part of an Achilles tendon while avoiding the calf muscle and the Achilles tendon.

* * * * *